(12) United States Patent (10) Patent No.: US 6,560,475 B1
Viswanathan (45) Date of Patent: May 6, 2003

(54) MICROCOIL DEVICE FOR LOCAL WIDE FIELD-OF-VIEW AND LARGE GAIN MAGNETIC RESONANCE IMAGING

(75) Inventor: Raju R. Viswanathan, Towson, MD (US)

(73) Assignee: Image-Guided Drug Delivery Systems, Inc., Minneapolis, MN (US)

( * ) Notice: Subject to any disclaimer, the term of this patent is extended or adjusted under 35 U.S.C. 154(b) by 0 days.

(21) Appl. No.: 09/532,667

(22) Filed: Mar. 21, 2000

Related U.S. Application Data

(63) Continuation-in-part of application No. 09/448,720, filed on Nov. 24, 1999, which is a continuation-in-part of application No. 09/131,031, filed on Aug. 7, 1998, now Pat. No. 6,272,370, which is a continuation-in-part of application No. 08/916,596, filed on Aug. 22, 1997, now Pat. No. 5,964,705.

(51) Int. Cl.$^7$ ................................................. A61B 5/05
(52) U.S. Cl. ........................ 600/410; 600/411; 600/421; 600/422; 600/423; 324/300; 324/301; 324/313; 324/318; 324/322
(58) Field of Search ................................ 600/407, 409, 600/410, 411, 419, 422, 423, 425, 427, 9–13; 604/19, 21; 607/101, 104; 324/300, 301, 313, 318, 322, 219

(56) References Cited

U.S. PATENT DOCUMENTS

| | | | | |
|---|---|---|---|---|
| 4,680,548 A | * | 7/1987 | Edelstein et al. | 324/318 |
| 5,180,982 A | * | 1/1993 | Zeiger | 324/318 |
| 5,427,103 A | * | 6/1995 | Fujio et al. | 600/101 |
| 5,659,281 A | * | 8/1997 | Pissanetzky et al. | 335/296 |
| 5,715,822 A | * | 2/1998 | Watkins | 128/899 |
| 5,986,454 A | * | 11/1999 | Leifer | 324/318 |
| 6,054,854 A | * | 4/2000 | Kawamoto | 324/318 |
| 6,266,551 B1 | * | 7/2001 | Osadchy et al. | 600/424 |
| 6,304,769 B1 | * | 10/2001 | Arenson et al. | 600/424 |

\* cited by examiner

Primary Examiner—Marvin M. Lateef
Assistant Examiner—Jeoyuh Lin
(74) Attorney, Agent, or Firm—Mark A. Litman & Assoc. P.A.

(57) ABSTRACT

Microcoil designs are provided that enable unique RF response Field profiles that are particularly useful in MRI imaging procedures, particularly where fields of view outside of the medical device are desirable. These devices are particulatly for use within an organism, the device comprising an element having at least one RF receiver, the coils of said microcoils defining a cross-section that lies in a plane oriented at 0 to 90 (or 0 to 80) degrees to the longest axis of the device. Another way of describing the device is as a device for use in an organism, the device comprising an element having at least one wound microcoil with at least three windings on the microcoil. Each winding has an aspect ratio of greater than one. The aspect ratio of each winding is measured as the ratio of longest to shortest dimension in a cross section situated approximately transverse to the winding axis of the coil windings, the winding axis also being transverse to the longest axis of said device. Another way of describing the device for use within an organism is as a device comprising an element having at least one RF receiver microcoil, the coils of the microcoils defining a cross-sectional contour having an alignment value of at least 0.75 with the longest axis of the device. The coil windings of the microcoil may have the cross-section comprise a geometric shape, such as a curvilinear shape, a polygon (regular or irregular), or a polygon where comers on the polygon are softened (e.g., slighly rounded). The device may comprise a catheter having at least one lumen. At least one microcoil should be located with its longest dimension defining a longitudinal spatial extent (direction) parallel to the at least one lumen and the coils having a conductor thickness of greater than 0.01 mm and less than 2.4 mm.

49 Claims, 6 Drawing Sheets

A view illustrating the microcoil geometry in relation to a medical device.

A view illustrating the microcoil geometry in relation to a medical device.

A plot of the logarithm of the transverse magnetic field profile at a section located at .02 times the coil length.

A plot of the logarithm of the transverse magnetic field profile at a section located at half the coil length.

MICROCOIL DEVICE FOR LOCAL WIDE FIELD-OF-VIEW AND LARGE GAIN MAGNETIC RESONANCE IMAGING

RELATED APPLICATIONS

This application is a continuation-in-part of U.S. patent application Ser. No. 09/448,720 filed on Nov. 24, 1999 and of U.S. patent application Ser. No. 09/131,031 filed Aug. 7, 1998 now U.S. Pat. No. 6,272,370 and in turn claims continuation-in-part status from U.S. patent application Ser. No. 08/916,596 filed Aug. 22, 1997, now U.S. Pat. No. 5,964,705.

BACKGROUND OF THE INVENTION

1. Field of the Invention

This invention relates to medical devices for the reception of radio frequency electromagnetic radiation. These devices are used to obtain a local but very wide field-of-view magnetic resonance image of a region within a natural organism (such as within a human) or elsewhere. Medical devices such as catheters and other devices for delivery of therapeutic agents and monitoring of metabolic activity may be used together with such magnetic resonance imaging devices. The use of novel microcoil configurations in the devices alter the response characteristics of the microcoils.

2. Background of the Art

Throughout this specification, the term MR is used to mean "Magnetic Resonance" and "MR microcoil" is used to denote a magnetic resonance device used for imaging from within a patient. MR coils are conventionally used externally to the body in order to generate MR images, while the MR microcoil may be mounted at the tip of a catheter or other insertion device used commonly to probe the interior of a body so as to provide quick and direct access to the region where imaging is required. It is essential during the course of medical procedures such as image-guided and minimal access surgery, performed within small regions of a patient's anatomy, to be able to visualize the procedure being performed by the surgeon and the neighborhood of the anatomical region being treated surgically. While several methods, including x-ray imaging and fiber optic viewing offer possible alternative means of performing the visualization, magnetic resonance imaging methods are a particularly convenient means of doing this, especially given the highly localized nature of the procedures being performed. Extended x-ray exposures are harmful to the patient, and fiber optic viewing is not well suited either to viewing within small confines or to volume visualization. Both of these limitations may be circumvented by magnetic resonance imaging.

In addition, as described in U.S. patent applications Ser. Nos. 8/857,043 and 08/856,894 filed on May 15, 1997, the use of improved Magnetic Resonance Imaging (MRI) techniques and devices enables a real-time visualization of compositional changes in the molecular composition of small regions within patients. The compositional changes may be caused by delivery of drugs or active chemicals, or by the stimulation of local chemical production by tissues or organs in the patient. MRI can actually enable visualization of minute concentration changes within the body, particularly intracranial regions of the patient.

U.S. Pat. No. 5,271,400 describes a tracking system for the position and orientation of an invasive device within a patient. The device includes a receiver coil and an MR active sample. In response to radio frequency radiation generated by an MR scanner system, the sample absorbs and re-emits this radiation as decaying radio frequency signals. The receiver picks up magnetic resonance signals re-emitted by the sample, from an analysis of which the location (position and orientation) of the device in space may be reconstructed. The frequencies are proportional to the location of the coil along the applied field gradients, since the signals are received in the presence of these magnetic field gradients. The system is designed to enable location of the invasive device and enhanced imaging of a region around the invasive device is not a functionality intended for this device.

In 'MR imaging of blood vessels with an intravascular coil', J. Mag. Res. Imag., 1992, Vol. 2, pages 421–429, A. J. Martin, D. B. Plewes and R. M. Henkelman describe an opposed solenoid design for an intravascular MR microcoil. This paper describes microcoils made of a pair of helical windings arranged in opposed fashion at the tip of a catheter, shown to be suitable for magnetic resonance imaging purposes. The term "opposed coil" means a coil in which the relative winding of two coil segments is opposite in sense, and the current flow in each opposed coil winds in opposite directions about the coil axis (relative to moving towards or away from the core or axis of the coil). That is, viewing the coils looking down an axis of the core around which the coils are disposed, one will be wrapped clockwise and the other will be wrapped counterclockwise, with a common lead between the two segments. The field-of-view of this coil is roughly cylindrical about the opposed solenoidal windings. The coil is essentially radio frequency insensitive beyond the longitudinal extent of the windings since the magnetic field in this design is squeezed out of the gap between the windings and is only significantly large in a cylindrical region that does not extend too far beyond this gap.

E. Atalar et al. describe a catheter receiver coil in 'High resolution MRI and MRS by using a catheter receiver coil',Mag. Res. Med., 1996, Vol. 36, pages 596–605. The gain of this coil falls off rapidly with distance from the coil so that noise levels in an image adjusted for the signal may still vary widely across the image. In addition, the gain (signal-to-noise ratio) provided by this design may be significantly improved upon by other means, such as in the invention described herein.

U.S. Pat. No. 5,271,400 describes a tracking system for the position and orientation of an invasive device within a patient. The device includes a receiver coil and an MR active sample. The receiver picks up magnetic resonance signals generated by the sample. The frequencies are proportional to the location of the coil along the applied field gradients, since the signals are received in the presence of these magnetic field gradients.

U.S. Pat. No. 4,572,198 describes a catheter for use with magnetic resonance imaging systems, the catheter including a wound coil for exciting a weak magnetic field at the catheter tip. This construction provides a local distortion of the MR image, yielding an image cursor on the magnetic resonance imaging display.

U.S. Pat. No. 5,964,705 describes an opposed solenoid design for an MR microcoil with helical winding's whose pitch varies along the length of the winding with the aim of achieving homogeneity. However, the optimization method given there for finding a suitable pitch variation assumes a 'sheet current'distribution of the current along the catheter tip, which may not be not realized in practice. Accordingly, the homogeneity of the field produced by the microcoil can be improved by other means, such as the invention described and claimed herein.

A copending, commonly assigned application, filed the same day as this application and bearing Attorneys' Docket No. 723.030US1 in the name of Raju Viswanathan, titled A Microcoil Device with a Forward Field-of-View for Large gain Magnetic Resonance Imaging" describes a microcoil configuration wherein a device to be inserted into a patient comprises a solid body having at least one microcoil physically associated with the solid body, each microcoil having an outside microcoil diameter of 6 mm or less and a common axis, with at least one microcoil physically associated with the solid body at a distal end, at least 50% of individual windings of said each microcoil intersecting a geometric plane perpendicular to said common axis.

Copending U.S. patent application Ser. No. 09/532,145, filed the same day as this Application, and titled "A DEVICE FOR HIGH GAIN AND UNIFORMLY LOCALIZED MAGNETIC RESONANCE IMAGING" discloses a microcoil configuration, preferably on a medical device to be inserted into a patient, that has an opposed pair of microcoils. At least one or each microcoil of the opposed pair of microcoils has at least a region where a diameter circumscribed by a first winding is greater than the diameter circumscribed by at least one complete adjacent second winding, especially an adjacent winding displaced from the first winding along an axis or core of the medical device or an axis of the microcoil. The second winding is nearer to or farther from an intermediate region between the microcoils that define the pair of microcoils. For example, it is common to have a connecting (usually straight or non-wound) lead between the two microcoils, and this lead may be used to define an intermediate region. The microcoil configuration with varying circumference between windings (especially adjacent windings) is generally referred to herein as a dumb-bell or horn configuration because of its general appearance and the individual microcoils are referred to as a horn microcoil, again because of the visual appearance of the microcoil.

In summary, while microcoils for such internal imaging have been described before, the said device here advances the art by virtue of being designed specifically to maximize the field of view as well as the signal gain within the field of view. This requires a tradeoff with homogeneity of the radial receptive field, which may however be corrected for if the receptive field (magnetic field B transverse to the main MR magnetic field produced by unit current in the coil) is known. This correction may be performed by dividing the reconstructed image intensity at a given pixel location by the gain corresponding to that pixel (which is proportional to the magnetic field B at that location), and repeating this for all pixels.

BRIEF DESCRIPTION OF THE INVENTION

Microcoil designs are provided that enable unique RF response Field profiles that are particularly useful in MRI imaging procedures, particularly where fields of view outside of the medical device are desirable. These devices are particulatly for use within an organism, the device comprising an element having at least one RF receiver, the coils of said microcoils defining a cross-section that lies in a plane oriented at 0 to 90 (or 0 to 80) degrees to the longest axis of the device. Another way of describing the device is as a device for use in an organism, the device comprising an element having at least one wound microcoil with at least three windings on the microcoil. Each winding has an aspect ratio of greater than one. The aspect ratio of each winding is measured as the ratio of longest to shortest dimension in a cross section situated approximately transverse to the winding axis of the coil windings, the winding axis also being transverse to the longest axis of said device Another way of describing the device for use within an organism is as a device comprising an element having at least one RF receiver microcoil, the coils of the microcoils defining a cross-sectional contour having an alignment value of at least 0.75 with the longest axis of the device. The device may have the cross-section comprise a geometric shape, such as a curvilinear shape, a polygon (regular or irregular), or a polygon where comers on the polygon are softened (e.g., slighly rounded). The device may comprise a catheter having at least one lumen. At least one microcoil should be located with its longest dimension defining a longitudinal spatial extent (direction) parallel to the at least one lumen and the coils having a conductor thickness of greater than 0.01 mm and less than 2.4 mm.

DETAILED DESCRIPTION OF THE INVENTION

Figure 1:
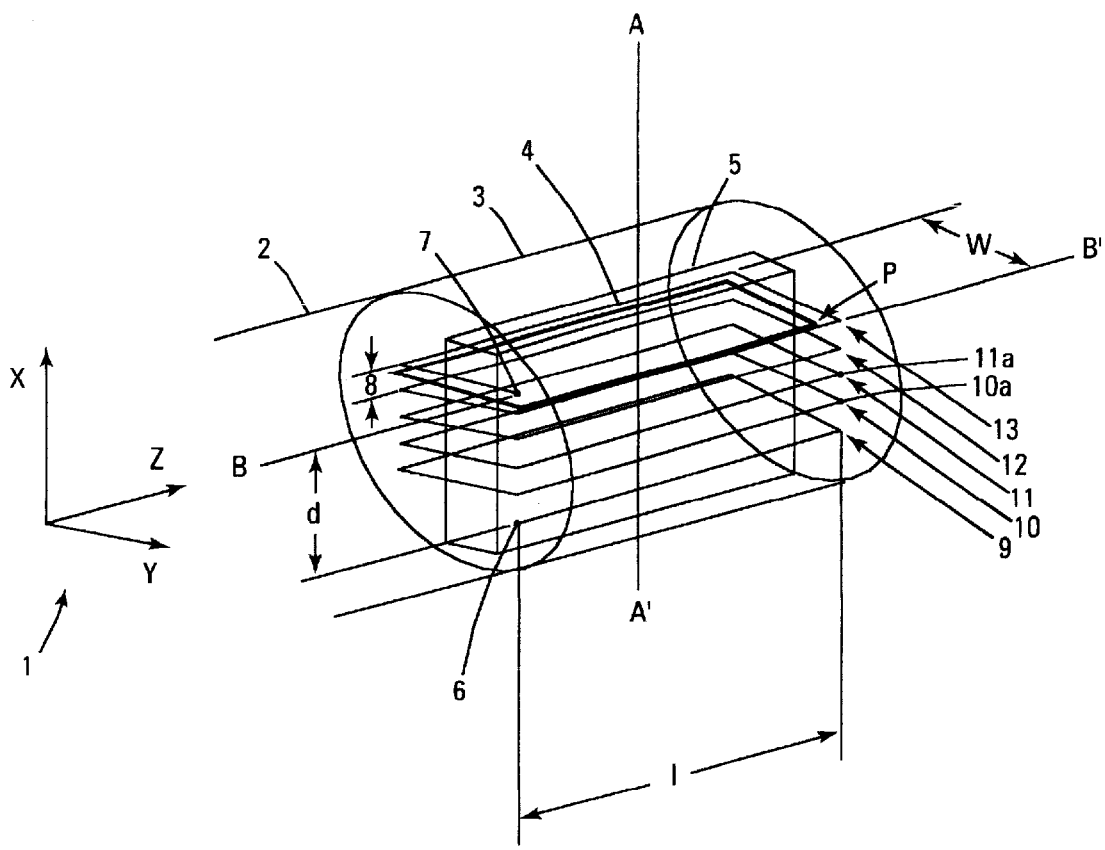
FIG. 1 shows a three dimensional plot of the microcoil geometry.

The detailed description in the following makes reference to the accompanying drawings which form a part hereof, which are included for non-limiting illustration of certain specific embodiments in which the invention may be practiced. These embodiments are described in sufficient detail to enable those skilled in the art to practice the invention, it is to be understood that other embodiments may be utilized and that structural, logical, physical, configurational, architectural and electrical changes may be made without departing from the spirit and scope of the present invention.

The practice of certain aspects of the present invention are applicable to all medical devices which might be used with magnetic resonance imaging-based viewing procedures occurring concurrently with the primary medical procedure. Features of the present invention which may individually have this general applicability within the medical device field include the types of RF-responsive coils and associated circuitry provided to medical devices to assure their MR-compatibility, and means and procedures for directing the microcoil within or with a catheter device. A preferred construction uses an MR Responsive coil having a significant distribution of surface area and orientation along an axis generally parallel to the major axis (longest dimension) of an underlying medical device, such as the tube length of a catheter or stent. In particular, the coil is wound such that the cross section of the winding transverse to the winding axis possesses a high aspect ratio. The winding axis is generally transverse to the long axis of the underlying medical device. By high aspect ratio, it is meant that when viewed along the axis about which the coil is wound, the coil presents a cross section in the form of a contour whose ratio of largest width to smallest width is at least 4. The microcoil may be wound in any configuration that presents a substantial distribution parallel to the body of a major axis of the medical device. A simple example of such a construction would be to have the microcoils rectangularly wound (especially with a high aspect ratio) about the device, for example, with the coil embedded within or attached to the outside of the catheter or other device, with the long side of the rectangle being parallel to the catheter axis. Thus the coil's winding axis is transverse (e.g., between 0 and 85 degrees, or between 0 and 60 degrees or between 0 and 30 degrees) to the catheter axis (e.g., from parallel to the catheter axis to the larger degree angle) (shown in FIG. 1 and further described below). The catheter axis is essentially the axis of the catheter along its longest dimension (usually the axis of the generally cylindrical body forming the catheter, shown as B–B' in FIG. 1). This winding geometry creates a large field of view transverse to the catheter axis.

One general description of the practice of the present invention is included in the following text. A device according to the invention includes its use within an organism, the device comprising an element having at least one wound microcoil with an aspect ratio larger than four the winding coils of said microcoils defining a polygonal cross-section of three to twelve sides, and the aspect ratio being defined as the ratio of largest diameter to smallest diameter of said polygonal section of said microcoil. By polygonal, it is not meant that the transition from one generally linear face to another generally linear face is necessarily a sharp angle, as there may be a generally polygonal shape with rounded transitions from one face to another. The term polygonal, unless restricted by the term "rigid polygonal" allows for generally polygonal shapes, e.g., a multiplicity of non-continuously arcing surfaces, and generally straight linear elements or faces, with rounded transitions between the generally straight linear elements or faces. For example, a square with its corners rounds up to forty percent of the length of each side would still be polygonal according to this definition. The term also includes cross-sections where the rounding of the edges extends 35% or less, 30% or less, 20% or less, 10% or less, and 5% or less of each side, and rigid polygonal shapes. The device may comprise a catheter having at least one lumen, and the at least one microcoil is located with its longest dimension defining a longitudinal spatial extent parallel to said at least one lumen while the conductor making up the coils has a thickness of greater than 0.01 mm and less than 2.4 mm. The device may include at least one drug delivery port present within it. The device may have the at least one drug delivery port located so that at least some drug which is delivered through said port is delivered away from the device within a volume bordered by planes extending transverse to the device at the ends of said longitudinal spatial extent. The device may have microcatheters present within the device. These may extend outside of the device to deliver at least some liquid material within a volume bordered by planes extending radially from the catheter at the ends of said longitudinal spatial extent. In response to radiofrequency transmission, the device may generate a reception field which has an average strength that diminishes by a factor of at least 10 from an area defined by a cylinder of 1.5 cm about a core axis of the cylindrical device to an area defined by a cylinder of 4.0 cm about the core axis of the cylindrical device. The device may have at least one high aspect ratio wound microcoil embedded within a binder material and may have the at least one high aspect ratio microcoil electrically connected to a preamplifier within a portion of the device which may be inserted into an organism. The device may also comprise an element having at least one high aspect ratio microcoil with its longest dimension transverse to its winding axis and defining a longitudinal spatial extent, the winding coils of said microcoils defining a polygonal cross-section of four to six sides.

Figure 5A:
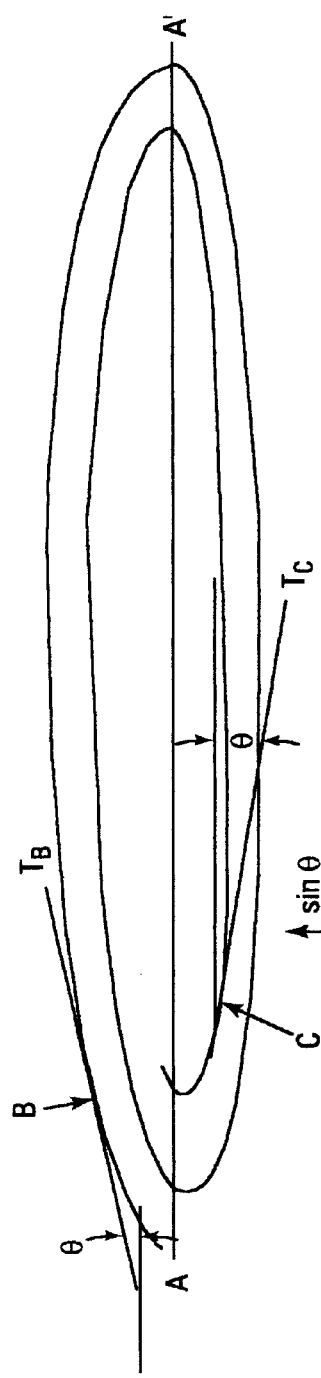
FIG. 5 shows some alternative winding constructions within the practice of the present invention.

A unique feature of the present invention is the high aspect ratio of the winding in a cross section transverse to the winding axis, which allows for a large receptive field in a roughly cylindrical region surrounding the catheter axis. The gain in this cylindrical region falls off with increasing distance from the catheter axis and can be very high within a cylindrical slab of diameter about 2 cm surrounding the catheter axis. Within this slab, the gain can be as much as 100 times larger than that correspondingly obtained from a typical head coil. This choice of winding geometry also yields a very homogeneous field profile along a direction parallel to the catheter axis. While a high-aspect-ratio rectangular shape for the winding pattern is most preferred, other high-aspect-ratio geometries may also be used. These alternative designs are shown in FIGS. 5 and 6. In FIG. 5, the aspect ratio would be the ratio of the length (Lo) to the width or diameter (w) of the particular winding. By high aspect ratio is meant that the ratio of length to diameter in a winding is at least 4, at least 5 or higher. Configuration a) shows the highest cosine profile and therefore the highest percent of the coil winding that would be aligned with the catheter axis (B–B'). The determination of the percentage of alignment of the winding with the catheter axis is determined by a formula later described herein. This configuration 5a) would provide a percentage alignment of about 90% or more.

Figure 5B:
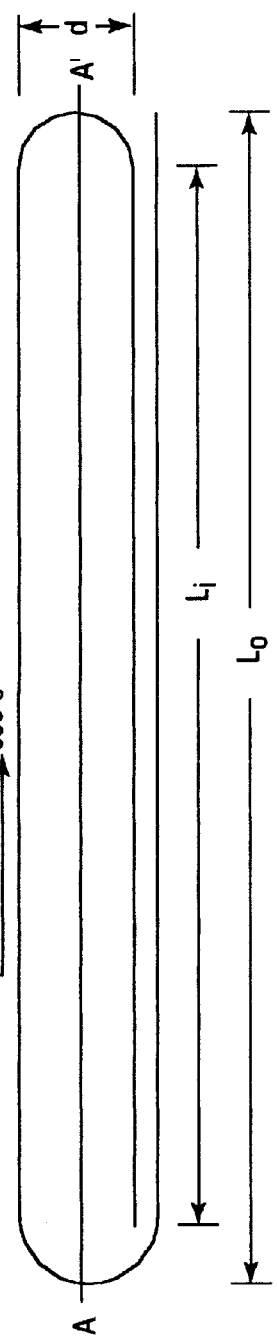
Figure 6:
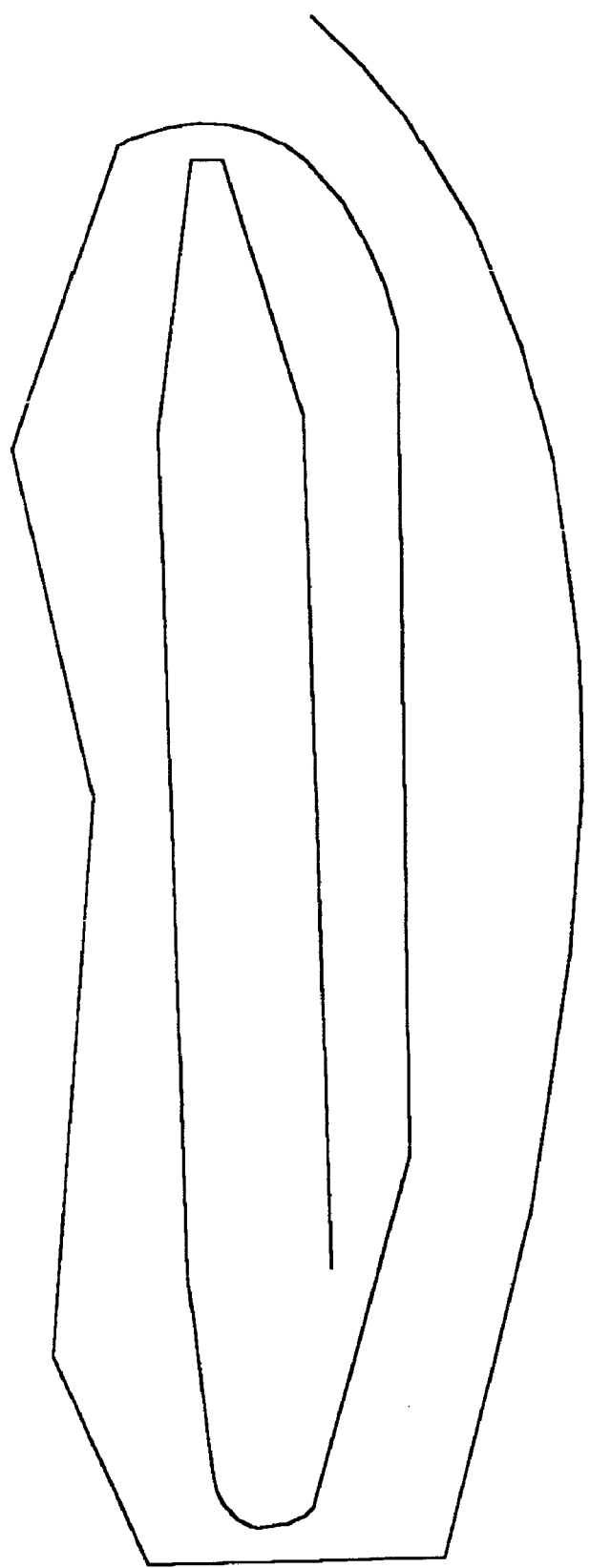
FIG. 6 also shows an alternative winding constructions within the practice of the present invention.

FIG. 5b) and 6 show other configurations that also provide for higher winding orientation with the catheter axis. These configurations 5b) and 6 show that regular polygon shapes are not essential and that curvilinear shapes and irregular shapes may be used. The integration of the function of the cosine over the surface of the wire is done with regard to the angle $\phi$, measured at each point along the winding (B and C, for example) with respect to the angle $\phi$ of the tangent T at that point (e.g., $T_C$ and $T_B$). Greater orientation of the wire of the microcoil and the winding along with the axis of the catheter A–A' increases the performance due to the field configuration according to the present invention.

One way of defining the distribution of the microcoils according to the present invention is as follows. When looking at a cross-section of each winding, if $\phi$ is the angle made by the tangent to the winding at each point on it with the long axis of the device (e.g., the axis of the catheter), the integration of the absolute value of the cosine of the winding (s) with respect to the long axis of the device must equal at least 0.75. That is, $$\text{Alignment Value (AV)} = \Sigma(|\cos\phi|)d\phi/\Sigma(d\phi)$$

with $\Sigma$ denoting an integral taken over the length of the entire winding. It is desirable that the alignment value equals, at least 0.70, at least 0.75, at least 0.80, at least 0.85, and at least 0.90. It is not possible to have an alignment value of exactly 100% because of the need for the return of the coil, but the closer the value to 100%, the more specific is the field generated from the design. This alignment value is with respect to the integration from 0 to $2\pi$ radians about each winding or all windings within the microcoil. This can be seen also in FIGS. 5 and 6, as herein explained. A circular winding would have an alignment value of $2/\pi$ (about 0.64).

A device for use within an organism according to the invention may comprise an element having at least one RF receiver microcoil, the coils of said microcoils defining a cross-sectional contour having an alignment value of at least 0.75 with the longest axis of the device.

There are certain terms used in the description of the present invention that should be defined to assist in a better understanding of the invention. A coil or microcoil is a set of wires or electrical elements forming a continuous conducting path around a device. The coils or microcoils comprise at least windings or wires that form the structural content of the coils or microcoils. The windings or wires have a thickness (which can be referred to as a diameter or cross-section of the wires, but will be referred to as a thickness) and the windings as they form the coils or microcoils form shapes that have a diameter (loci of distances) about a core or axis of the microcoils. In the practice of the present invention, this axis of the microcoils is transverse to the approximate axis or core of the device carrying the windings. The space between adjacent windings can be measured in three different ways.

One general description of the present invention may be as a device for use within an organism, the device comprising an element having at least one highaspect ratio microcoil, with the aspect ratio (defined as the ratio of longest to shortest dimension) measured in a cross section transverse to the coil's winding axis, and the winding axis being perpendicular to the core axis of the device. The device may, for example, comprise, in addition to the microcoil a catheter having at least one lumen. A particularly useful device has at least one drug delivery port present within said device. The at least one microcoil may be situated just abutting (in front of, under, or behind) at least one port hole on the catheter. The windings may have a conductor thickness greater than 0.01 mm and at least some of the windings may have a short-side diameter of greater than 0.1 mm and less than 4.0 mm or less than 2.4 mm. A particularly good location for the at least one drug delivery port is a position where at least some drug which is delivered through the port is delivered away from the device within a space or volume bordered by planes at the proximal and distal ends of the microcoil extending transversely to the device. One additional design benefit is to have at least some microcatheters present within said device which extend outside of said device to deliver at least some liquid material within said volume bordered by transverse planes at proximal and distal ends of the microcoil The volume where the liquid material could be easily visualized extends to a distance of about 2 cm radially outward from the catheter axis, thereby defining an anuular volume around the catheter. At the outer edge of a cylindrical region of diameter 4 cm surrounding the microcoil, the gain is comparable to that obtained from a typical head coil. The entire field of view of the microcoil is then a roughly cylindrical region of diameter 4 cm surrounding the microcoil, within most of which the gain is substantially larger than that obtainable from a typical head coil. This field of view is also significantly larger than that for other microcoil designs (alluded to in the Background section herein) of comparable overall dimensions. The combination of wide field of view and the very high sensitivity of the coil in a significantly large region within the field of view represent a substantial advance in the design of magnetic resonance microcoils.

Besides the monitoring of small quantities of locally delivered therapeutic agents, including those used in gene and cell based therapies, an important application area of the microcoil described herein is the monitoring of cell and tissue function by means of magnetic resonance spectroscopy methods. These methods directly measure metabolic activity in tissue.

FIG. 1 shows a three dimensional view of the preferred microcoil geometry where the rectangular geometry of the winding is apparent. In FIG. 1, a coordinate system (also shown as 1) is chosen such that the z-axis is parallel to the long side of the coil (or to the catheter axis B–B').

The winding axis A–A' of the microcoil is parallel to the x-axis. The figure shows the microcoil 4 as consisting of five (5) complete turns of winding (9, 10, 11, 12 and 13) between the coil terminals 6 and 7, about the coil axis A–A', with uniform spacing (shown as 8) between adjacent turns. We will call the dimension of the entire wound coil in the y-direction with the width w of the coil and the dimension of the entire coil in the x-direction the depth d of the coil. The width of the coil is the smallest diameter presented by the coil in a section transverse to the winding axis, including the thickness of the conductor. The depth of the coil is the sum of (a) all the spacing distances between successive turns of winding and (b) the product of the number of winding turns and the conductor thickness. The aspect ratio of the microcoil 4 is the ratio (l/w). The length l of the coil (longest dimension in the z-direction) may vary in the range 0.5 cm to 6 cm and may more preferably lie between 1 cm and 4 cm. The width w of the coil, chosen so as to fit within a catheter or affixed to the outside of a catheter, may range from 0.5 mm to 6 mm, and more preferably may lie between 1 mm and 4 mm. The depth d of the entire coil (including all the winding turns and the spaces between them) may range from 0.3 to 6 mm, and more preferably may lie between 1 mm and 4.5 mm. The conductor used in the winding may be electrically highly conducting material such as copper, silver or gold, or it may be suitable alloys, composites or plated combinations of conducting materials. The thickness of the conductor used in the windings may range from 0.01 mm to 2 mm and the gap between adjacent turns of conductor may be between 0.01 mm and 1.5 mm. The number of turns in the winding may, for non-limiting example only, vary between one and fifteen, between one and ten, between two and ten, between two and eight, between three and ten and between three and eight.

The sensitivity or gain of the coil is proportional to the component of the magnetic field that is transverse to the main field of a magnetic resonance imaging system, produced by unit current flowing through the coil. We compute below the magnetic field transverse to the main field of a magnetic resonance system and produced by unit current in the microcoil for the case when its long axis is parallel to the main magnetic field. For other orientations of the microcoil with respect to the main field the magnetic field may be obtained by an appropriate rotation. The magnetic field may be determined in a specified region surrounding the coil by using the Biot-Savart law:

$$B = (\mu/4\pi)\Sigma[(dl \times r)/(|r|^3)]$$

with the integral $\Sigma$ taken over the entire length L of the conductor in the coil, where B is the magnetic field at a specified point in space, dl is a current-carrying length element and r is the distance vector from the current element to the specified point.

A study of the distribution of the magnetic field around the coil is useful for assessing the field profile. In particular, with the choice of coil orientation with respect to the main magnetic field of the imaging system as stated above, it is the component of the magnetic field transverse to the main magnetic field that is relevant for signal construction. For this purpose, we have therefore mapped the transverse component of the magnetic field along sections transverse to the catheter axis, at various locations along the coil length.

Figure 2:
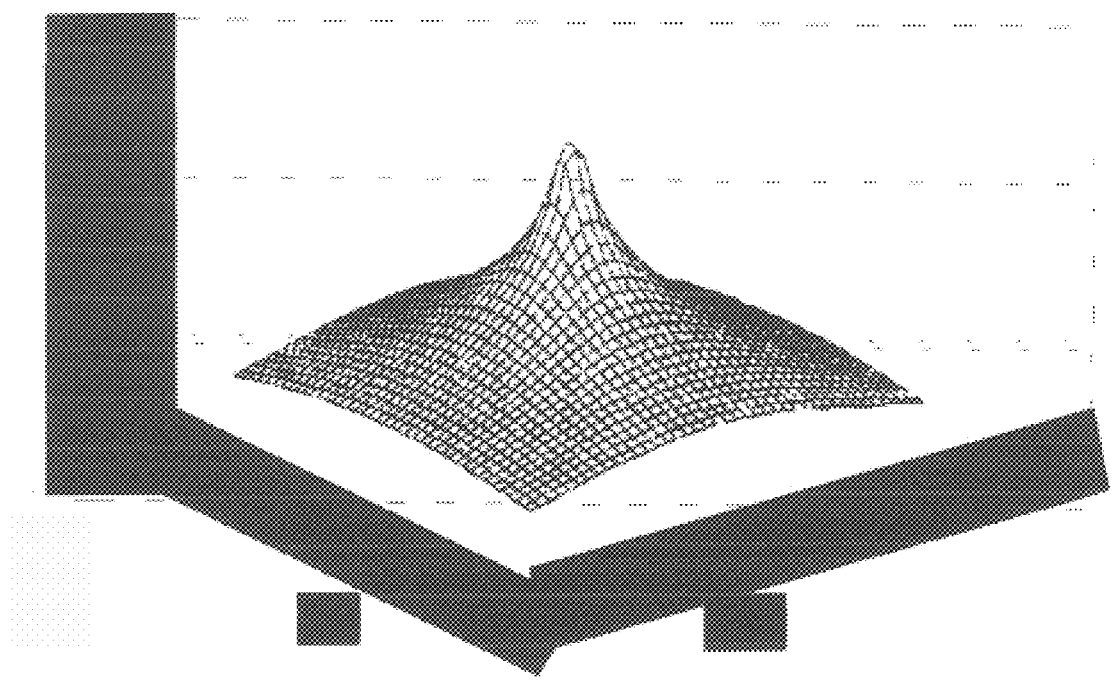
FIG. 2 shows a semi-logarithmic plot of the transverse magnetic field profile at a given cross section (at two-tenths of the coil length) through the microcoil.

FIG. 2 is a plot of the logarithm of the transverse magnetic field in a 4 cm×4 cm transverse section located at a distance of 20% along the coil length measured from the end of the catheter with the coil terminals at that end. The five-turn coil shown in FIG. 1 with approximate dimensions l=2 cm, w=2 mm, d=1.5 mm was used in this computation. The transverse field is very sharply peaked at the center and consequently we have illustrated the field profile in a logarithmic plot. The significance of the plot is that the transverse field profile, and thence the sensitivity, is still substantial at the outer edges of this section.

Figure 3:
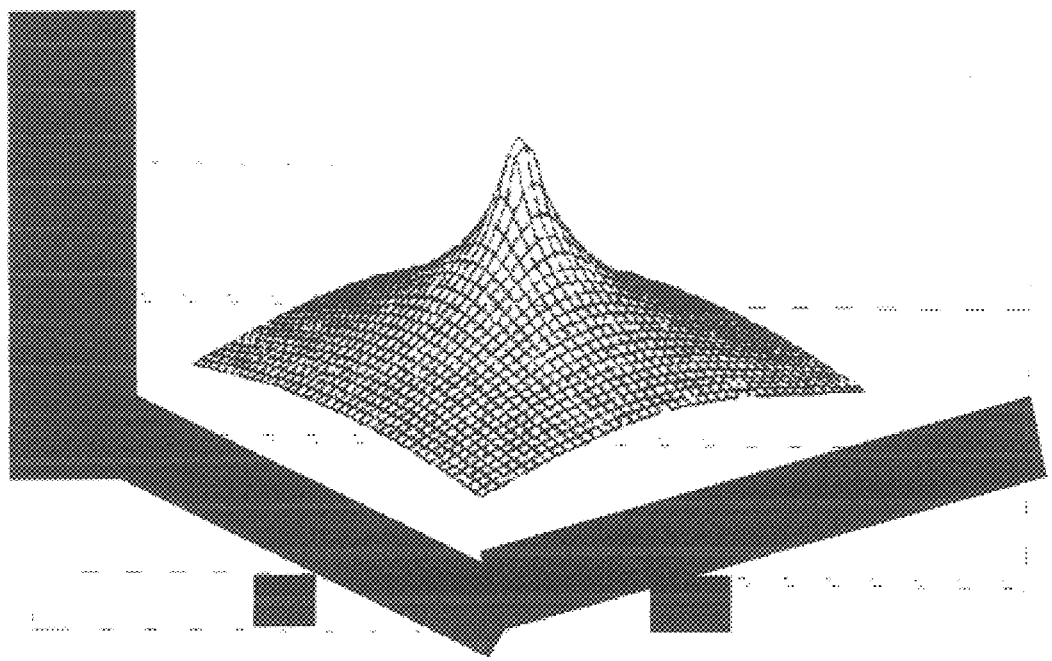
FIG. 3 shows a semi-logarithmic plot of the transverse magnetic field at a transverse cross section passing through the middle of the microcoil.

FIG. 3 is similar to FIG. 2 except that it is the transverse field profile at a section located at the middle of the coil. It is evident from these two figures that the field profile changes very little along the length of the coil.

Figure 4:
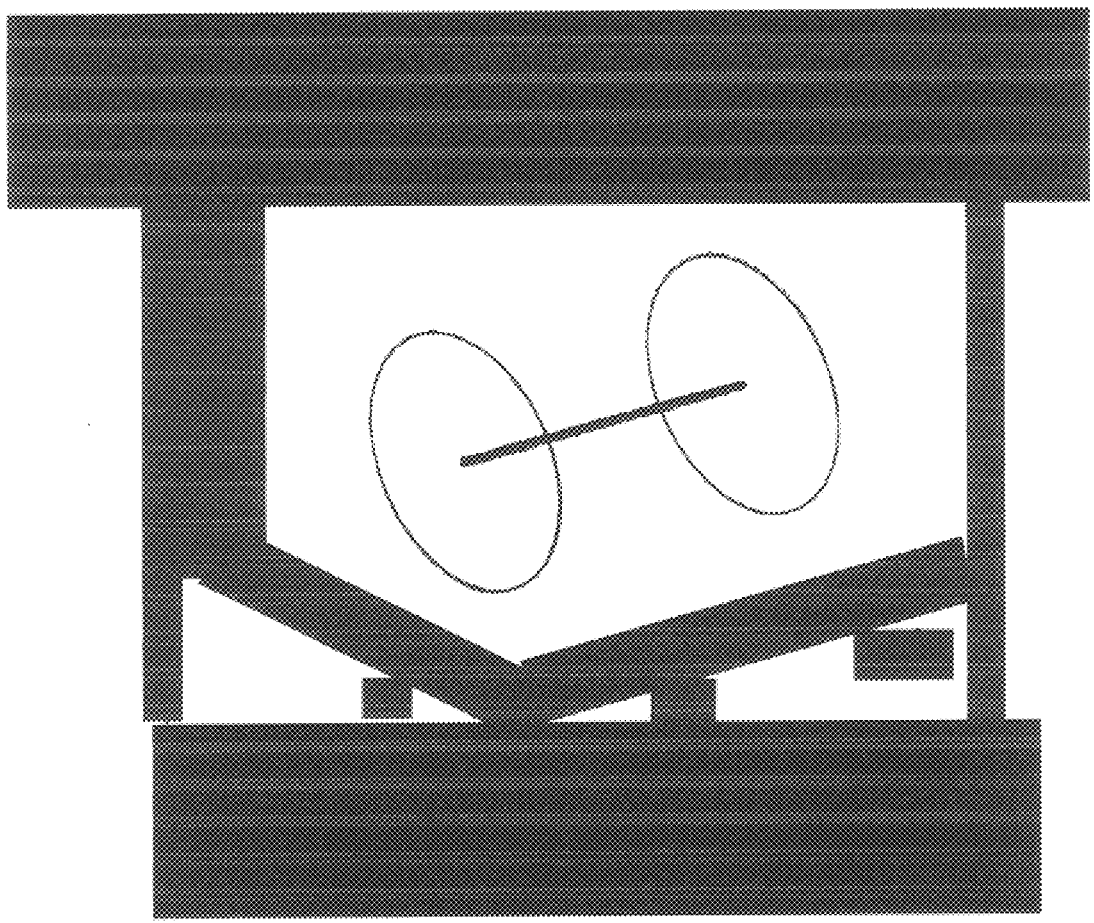
FIG. 4 shows a depiction of the field of view of the microcoil in comparison to its size.

FIG. 4 shows the size of the sensitive region in relation to that of the coil itself. The ends of the cylinder bounding this cylindrical region are shown. The signal-to-noise ratio at the edge of this region is comparable to that obtained from a typical head coil used in magnetic resonance imaging.

FIGS. 5 and 6 show possible variations in the winding pattern which may be followed.

The fabrication of the coil may be accomplished using many different methods familiar to those skilled in the art, including winding conducting wires or filaments of wire, sputtering, deposition and etching processes, masked deposition, microlithography, and such other techniques known to practitioners of the art, on different substrates, including flexible films, and possibly followed by folding of individual layers of the circuitry to achieve the final configuration of the coil geometry. For example, a sheet may have individual coil lines or wires provided therein, and the sheet may be wrapped or folded to provide the desired circuitry design. As stated earlier, the conductor may be of copper, silver, gold or other electrically highly conducting material possibly including alloys, composites or platings. The coil itself may be enclosed by or encased within tightly fitting protective or insulating material such as a polymer. If deposited on a substrate of polymer film, the film may be rolled around a polymer core in order to yield a mechanically rigid geometry. If a single strip of film is used as substrate, the ends of conducting strips deposited on the film strip may be microsoldered together in order to make up a continuous wound conductor. Through holes or posts may be use to connect circuitry on various layers.

The specific geometry of the leads connecting to the microcoil may be fashioned in such a manner as may be convenient for the specific application for which the invention is used.

What is claimed:

1. A device for use within an organism, said device comprising an element having at least one RF receiver having at least one wound microcoil with at least one coil having at least three windings in the at least one coil, the coils of said at least one microcoil defining a cross section that lies in a plane oriented at 0–80 degrees to the longest axis of the device, said windings having an aspect ratio of greater than one.

2. A device for use in an organism, the device having a longest axis, said device comprising an element having at least one wound microcoil with at least three coil windings on the at least one wound microcoil, each coil winding having an aspect ratio of greater than one, the aspect ratio of each coil winding being measured as the ratio of longest to shortest dimension in a cross section situated transverse to the winding axis of the coil windings, said winding axis also being transverse to the longest axis of said device.

3. The device of claim 2 where said cross-section comprises a geometric shape.

4. The device of claim 3 wherein said shape comprises a polygon.

5. The device of claim 3 where said cross-section comprises a geometric shape.

6. The device of claim 5 wherein the geometric shape comprises a curvilinear shape.

7. The device of claim 6 wherein said device comprises a catheter having at least one lumen, and said at least one microcoil located with its longest dimension defining a longitudinal spatial extent parallel to said at least one lumen and said coils have a conductor thickness of greater than 0.01 mm and less than 2.4 mm.

8. The device of claim 5 wherein said shape comprises a polygon.

9. The device of claim 8 wherein said device comprises a catheter having at least one lumen, and said at least one microcoil located with its longest dimension defining a longitudinal spatial extent parallel to said at least one lumen and said coils have a conductor thickness of greater than 0.01 mm and less than 2.4 mm.

10. The device of claim 9 wherein at least one drug delivery port is present within said device.

11. The device of claim 10 wherein said at least one drug delivery port is located so that at least some drug which is delivered through said port is delivered away from said device within said longitudinal spatial extent of said microcoil.

12. The device of claim 5 wherein said device comprises a catheter having at least one lumen, and said at least one microcoil located with its longest dimension defining a longitudinal spatial extent parallel to said at least one lumen and said coils have a conductor thickness of greater than 0.01 mm and less than 2.4 mm.

13. The device of claim 12 wherein at least one drug delivery port is present within said device.

14. The device of claim 12 wherein said at least one drug delivery port is located so that at least some drug which is delivered through said port is delivered away from said device within said longitudinal spatial extent of said microcoil.

15. The device of claim 12 wherein microcatheters are present within said device which extend outside of said device to deliver at least some liquid material within a volume bordered by planes extending radially from the catheter at ends of said longitudinal spatial extent of said microcoil.

16. The device of claim 12 wherein said device is cylindrical, and in response to radiofrequency transmission, generates a reception field which has an average strength that diminishes by a factor of at least 10 from an area defined by a cylinder of 1.5 cm about a core axis of said cylindrical device to an area defined by a cylinder of 4.0 cm about the core axis of said cylindrical device.

17. The device of claim 12 wherein said at least one microcoil is embedded within a binder material.

18. The device of claim 12 wherein said at least one microcoil is electrically connected to a preamplifier within a portion of said device which may be inserted into an organism.

19. The device of claim 2 wherein said device comprises a catheter having at least one lumen, and said at least one microcoil located with its longest dimension defining a longitudinal spatial extent parallel to said at least one lumen and said coils have a conductor thickness of greater than 0.01 mm and less than 2.4 mm.

20. The device of claim 19 wherein at least one drug delivery port is present within said device.

21. The device of claim 19 wherein said at least one drug delivery port is located so that at least some drug which is delivered through said port is delivered away from said device within said longitudinal spatial extent of said microcoil.

22. The device of claim 19 wherein microcatheters are present within said device which extend outside of said device to deliver at least some liquid material within a volume bordered by planes extending radially from the catheter at ends of said longitudinal spatial extent of said microcoil.

23. The device of claim 19 wherein said device is cylindrical, and in response to radiofrequency transmission, generates a reception field which has an average strength that diminishes by a factor of at least 10 from an area defined by a cylinder of 1.5 cm about a core axis of said cylindrical device to an area defined by a cylinder of 4.0 cm about the core axis of said cylindrical device.

24. The device of claim 19 wherein said at least one microcoil is embedded within a binder material.

25. The device of claim 19 wherein said at least one microcoil is electrically connected to a preamplifier within a portion of said device which may be inserted into an organism.

26. A device for use within an organism, said device comprising an element having at least one RF receiver microcoil, the coils of said microcoils defining a cross-sectional contour having an alignment value of at least 0.75 with the longest axis of the device.

27. device of claim 3 wherein the geometric shape comprises a curvilinear shape.

28. The device of claim 27 wherein said device comprises a catheter having at least one lumen, and said at least one microcoil located with its longest dimension defining a longitudinal spatial extent parallel to said at least one lumen and said coils have a conductor thickness of greater than 0.01 mm and less than 2.4 mm.

29. The device of claim 28 wherein at least one drug delivery port is present within said device.

30. The device of claim 28 wherein said at least one drug delivery port is located so that at least some drug which is delivered through said port is delivered away from said device within said longitudinal spatial extent of said microcoil.

31. The device of claim 28 wherein microcatheters are present within said device which extend outside of said device to deliver at least some liquid material within a volume bordered by planes extending radially from the catheter at ends of said longitudinal spatial extent of said microcoil.

32. The device of claim 28 wherein said device is cylindrical, and in response to radiofrequency transmission, generates a reception field which has an average strength that diminishes by a factor of at least 10 from an area defined by a cylinder of 1.5 cm about a core axis of said cylindrical device to an area defined by a cylinder of 4.0 cm about the core axis of said cylindrical device.

33. The device of claim 28 wherein said at least one microcoil is embedded within a binder material.

34. The device of claim 28 wherein said at least one microcoil is electrically connected to a preamplifier within a portion of said device which may be inserted into an organism.

35. The device of claim 26 wherein said device comprises a catheter having at least one lumen, and said at least one microcoil located with its longest dimension defining a longitudinal spatial extent parallel to said at least one lumen and said coils have a conductor thickness of greater than 0.01 mm and less than 2.4 mm.

36. The device of claim 35 wherein at least one drug delivery port is present within said device.

37. The device of claim 36 wherein said at least one drug delivery port is located so that at least some drug which is delivered through said port is delivered away from said device within said longitudinal spatial extent of said microcoil.

38. The device of claim 35 wherein microcatheters are present within said device which extend outside of said device to deliver at least some liquid material within a volume bordered by planes extending radially from the catheter at ends of said longitudinal spatial extent of said microcoil.

39. The device of claim 35 wherein said device is cylindrical, and in response to radiofrequency transmission, generates a reception field which has an average strength that diminishes by a factor of at least 10 from an area defined by a cylinder of 1.5 cm about a core axis of said cylindrical device to an area defined by a cylinder of 4.0 cm about the core axis of said cylindrical device.

40. The device of claim 35 wherein said at least one microcoil is embedded within a binder material.

41. The device of claim 35 wherein said at least one microcoil is electrically connected to a preamplifier within a portion of said device which may be inserted into an organism.

42. The device of claim 4 wherein said device comprises a catheter having at least one lumen, and said at least one microcoil located with its longest dimension defining a longitudinal spatial extent parallel to said at least one lumen and said coils have a conductor thickness of greater than 0.01 mm and less than 2.4 mm.

43. The device of claim 42 wherein at least one drug delivery port is present within said device.

44. The device of claim 42 wherein said at least one drug delivery port is located so that at least some drug which is delivered through said port is delivered away from said device within said longitudinal spatial extent of said microcoil.

45. The device of claim 42 wherein microcatheters are present within said device which extend outside of said device to deliver at least some liquid material within a volume bordered by planes extending radially from the catheter at ends of said longitudinal spatial extent of said microcoil.

46. The device of claim 42 wherein said device is cylindrical, and in response to radiofrequency transmission, generates a reception field which has an average strength that diminishes by a factor of at least 10 from an area defined by a cylinder of 1.5 cm about a core axis of said cylindrical device to an area defined by a cylinder of 4.0 cm about the core axis of said cylindrical device.

47. The device of claim 42 wherein said at least one microcoil is embedded within a binder material.

48. The device of claim 42 wherein said at least one microcoil is electrically connected to a preamplifier within a portion of said device which may be inserted into an organism.

49. A device for use within an organism, said device comprising an element having at least one RF receiver microcoil with wound coils, with the microcoils longest dimension defining a longitudinal spatial direction, the wound coils of said microcoils defining a cross-sectional contour having an alignment value of at least 0.75 with the longest axis of the device, with the number of turns of said winding coils comprising at least one full turn.

* * * * *